United States Patent
Yada et al.

(10) Patent No.: US 7,214,816 B2
(45) Date of Patent: May 8, 2007

(54) PROCESS FOR PRODUCING (METH)ACRYLIC ACID AND (METH)ACRYLIC ESTERS

(75) Inventors: Shuhei Yada, Yokkaichi (JP); Kenji Takasaki, Yokkaichi (JP); Yasushi Ogawa, Yokkaichi (JP); Yoshiro Suzuki, Yokkaichi (JP)

(73) Assignee: Mitsubishi Chemical Corporation, Tokyo (JP)

( * ) Notice: Subject to any disclaimer, the term of this patent is extended or adjusted under 35 U.S.C. 154(b) by 306 days.

(21) Appl. No.: 11/027,685

(22) Filed: Jan. 3, 2005

(65) Prior Publication Data

US 2005/0267309 A1     Dec. 1, 2005

Related U.S. Application Data

(63) Continuation of application No. PCT/JP04/15696, filed on Oct. 22, 2004.

(30) Foreign Application Priority Data

May 27, 2004    (JP) .............................. 2004-158095

(51) Int. Cl.
*C07C 67/00*    (2006.01)
*C07C 51/16*    (2006.01)

(52) U.S. Cl. ..................... 560/208; 562/545

(58) Field of Classification Search ............... None
See application file for complete search history.

(56) References Cited

FOREIGN PATENT DOCUMENTS

| | | |
|---|---|---|
| JP | 2001-58970 | 3/2001 |
| JP | 2001-213839 | 8/2001 |
| WO | WO 03/051810 A1 | 6/2003 |

*Primary Examiner*—Paul A. Zucker
(74) *Attorney, Agent, or Firm*—Nixon & Vanderhye P.C.

(57) ABSTRACT

There is provided a process for producing (meth)acrylic acid and (meth)acrylic esters, which can be operated in a continuous and stable manner for a long period of time.

1 Claim, No Drawings

PROCESS FOR PRODUCING (METH)ACRYLIC ACID AND (METH)ACRYLIC ESTERS

This application is a CON of PCT/JP04/15696 filed Oct. 22, 2004.

TECHNICAL FIELD

The present invention relates to a process for producing (meth)acrylic acid and (meth)acrylic esters, more particularly, to a process for producing (meth)acrylic acid and (meth)acrylic esters comprising the steps of (A) producing crude (meth)acrylic acid; (B) purifying the resultant crude (meth)acrylic acid to produce a (meth)acrylic acid product; and (C) reacting the crude (meth)acrylic acid with alcohol to produce (meth)acrylic esters, wherein when a plant used in any one of the steps (B) and (C) disposed in parallel with each other is stopped, the resultant surplus crude (meth)acrylic acid from the step (A) is temporarily stored in a tank, and when the stopped plant is restored, the crude (meth)acrylic acid stored in the tank can be treated without any change in an operational load of the plant used in the step (A).

BACKGROUND ARTS

The general method for producing (meth)acrylic acid includes a step (A) of reacting propane, propylene, or isobutylene and/or (meth)acrolein, with molecular oxygen or a molecular oxygen-containing gas by gas-phase catalytic oxidation method, adding a reaction gas containing the resultant (meth)acrylic acid in water to prepare an aqueous solution thereof, and then removing low-boiling components such as water and acetic acid from the aqueous solution to obtain crude (meth)acrylic acid; and a step (B) of purifying the resultant crude (meth)acrylic acid to obtain a (meth)acrylic acid product. Further, the (meth)acrylic acid produced by the above method is reacted with alcohol in a step (C) to produce (meth)acrylic esters.

In general, the crude (meth)acrylic acid produced in the above step (A) is sufficiently usable as raw (meth)acrylic acid for production of the (meth)acrylic esters. For this reason, a method in which a part of the crude (meth)acrylic acid produced in the step (A) is fed to the step (B) for producing the (meth)acrylic acid product therefrom, whereas a remainder of the crude (meth)acrylic acid is fed to the step (C) for producing the (meth)acrylic esters therefrom, has been preferably conducted from the standpoints of good production efficiency of the respective products as well as economical merits such as low installation costs.

As described above, in the case where the crude (meth)acrylic acid obtained in the plant used in the step (A) is fed to the plants used in the steps (B) and (C) disposed in parallel with each other, when any one of the plants used in the steps (B) and (C) is stopped owing to failure thereof, the crude (meth)acrylic acid to be fed to the stopped plant is temporarily stored in a tank, thereby enabling the other steps to be operated continuously.

As the conventional method for consuming the crude (meth)acrylic acid stored in the tank, there is known such a method in which the amount of the crude (meth)acrylic acid fed from the plant used in the step (A) to the plants used in the steps (B) and (C) is reduced by lowering an operation load of the plant used in the step (A), and the crude (meth)acrylic acid stored in the tank is fed to the plants used in the steps (B) and (C) in such an amount corresponding to the reduction in amount of the crude (meth)acrylic acid fed from the plant used in the step (A), thereby controlling the amount of the crude (meth)acrylic acid stored in the tank. This is because the operation capacity of the plant used in the step (A) has been conventionally designed so as to be identical to or slightly larger than a total operation capacity of the plants used in the steps (B) and (C) in the consideration of future expansion of amount of products produced. More specifically, since the amount of the crude (meth) acrylic acid produced in the step (A) is identical to or larger than the amount of the crude (meth)acrylic acid consumed in the steps (B) and (C), it has been conventionally required to reduce the operational load of the plant used in the step (A) in order to treat the surplus crude (meth)acrylic acid stored in the tank.

However, if the operational load of the plant used in the step (A) is varied, for example, if the operational load of a distillation column used in the step (A) for removal of low-boiling components is varied, the (meth)acrylic acid tends to be polymerized in the distillation column, resulting in troubles such as clogging due to resultant polymers thereof. In particular, in the case where an aqueous acrylic acid solution is distilled in an azeotropic separation column in the presence of an azeotropic solvent, the distillation procedure tends to be adversely affected by the variation in operational load of the column.

As the method of stably operating the distillation column for a long period of time, while preventing occurrence of clogging due to polymerization therein even if the operational load of the distillation column is varied, there is known such a method in which upon reduced operation where the amount of (meth)acrylic acid produced is reduced by α % as compared to that under ordinary operation conditions, the flow amount of liquid/gas within the distillation column is controlled to (100−α/2)% or more relative to a flow amount under the ordinary operation conditions (for example, Japanese Patent Application Laid-open No. 2003-183219). However, in the above method, since the operational load is also varied, occurrence of defects due to the varied operational load is inevitable.

Accordingly, hitherto, it has been demanded to provide a method capable of treating the crude (meth)acrylic acid temporarily stored in the tank when the step (B) or (C) is stopped without any substantial change in operational load of the step (A).

PROBLEM TO BE SOLVED BY THE INVENTION

The present invention has been made for solving the above conventional problems. An object of the present invention is to provide a process for producing (meth)acrylic acid and (meth)acrylic esters comprising the steps of:

(A) reacting propane, propylene, or isobutylene and/or (meth)acrolein, with molecular oxygen or a molecular oxygen-containing gas by gas-phase catalytic oxidation method to produce crude (meth)acrylic acid;

(B) purifying the resultant crude (meth)acrylic acid to produce a (meth)acrylic acid product; and (C) reacting the crude (meth)acrylic acid with alcohol to produce (meth)acrylic esters, wherein when a plant used in any one of the steps (B) and (C) disposed in parallel with each other is stopped, a resultant surplus crude (meth)acrylic acid is temporarily stored in a tank, and when the stopped plant is restored, the crude (meth)acrylic acid stored in the tank can be treated without any change in operational load of the plant used in the step (A).

MEANS FOR SOLVING PROBLEM

As a result of the present inventors' earnest studies for solving the above problems, it has been found that if a production capacity of the plant used in the step (A) is designed so as to be lower than a total consumption capacity of the plants used in the steps (B) and (C), the crude (meth)acrylic acid stored in the tank can be suitably treated in the plants used in the steps (B) and (C) without any substantial change in operation load of the plant used in the step (A).

The present invention has been attained on the basis of the above finding. To accomplish the aim, in an aspect of the present invention, there is provided a process for producing (meth)acrylic acid and (meth)acrylic esters comprising the steps of:

(A) reacting propane, propylene, or isobutylene and/or (meth)acrolein, with molecular oxygen or a molecular oxygen-containing gas by gas-phase catalytic oxidation method to produce crude (meth)acrylic acid;

(B) purifying the resultant crude (meth)acrylic acid to produce a (meth)acrylic acid product; and (C) reacting the crude (meth)acrylic acid with alcohol to produce (meth)acrylic esters, in case of stopping a plant used in any one of the steps (B) and (C) disposed in parallel with each other, a resultant surplus crude (meth)acrylic acid being temporarily stored in a tank, and after restoring the stopped plant, the crude (meth)acrylic acid stored in a tank being fed to the plant used in the step (B) and/or the plant used in the step (C), wherein a production capacity of the plant used in the step (A) is designed so as to be lower than a total consumption capacity of the plants used in the steps (B) and (C).

EFFECT OF THE INVENTION

In the process for producing (meth)acrylic acid and (meth)acrylic esters according to the present invention, which comprises the steps of (A) producing crude (meth)acrylic acid; (B) purifying the resultant crude (meth)acrylic acid to produce a (meth)acrylic acid product; and (C) reacting the crude (meth)acrylic acid with alcohol to produce (meth)acrylic esters, wherein when a plant used in any one of the steps (B) and (C) disposed in parallel with each other is stopped, a resultant surplus crude (meth)acrylic acid is temporarily stored in a tank, and the crude (meth)acrylic acid stored in the tank can be treated without any change in operational load of the plant used in the step (A) upon restoring the stopped plant.

PREFERRED EMBODIMENT FOR CARRYING OUT THE INVENTION

The present invention is described in detail below. The process for producing (meth)acrylic acid and (meth)acrylic esters according to the present invention includes the steps of (A) reacting propane, propylene, or isobutylene and/or (meth)acrolein, with molecular oxygen or a molecular oxygen-containing gas by gas-phase catalytic oxidation method to produce crude (meth)acrylic acid; (B) purifying the resultant crude (meth)acrylic acid to produce a (meth)acrylic acid product; and (C) reacting the crude (meth)acrylic acid with alcohol to produce (meth)acrylic esters. The steps (B) and (C) are provided subsequent to the step (A), and disposed in parallel with each other. A part of the crude (meth)acrylic acid produced in the step (A) is fed to the above step (B) for producing the (meth)acrylic acid product therefrom, whereas a remainder of the crude (meth)acrylic acid is fed to the step (C) for producing the (meth)acrylic esters therefrom.

In the production process of the present invention, in the case where the plant used in any one of the steps (B) and (C) is stopped, it is required to temporarily store the crude (meth)acrylic acid to be fed to the stopped plant in a tank. The tank is connected to the respective plants used in the steps (A), (B) and (C) through conduits. When any one of the plants used in the steps (B) and (C) is stopped, the crude (meth)acrylic acid is fed to the tank from the plant used in the step (A). After the stopped plant is restored, the crude (meth)acrylic acid stored in the tank can be fed to the plant used in the step (B) and/or the plant used in the step (C).

First, the step (A) is explained. In the step (A), propane, propylene, or isobutylene and/or (meth)acrolein is reacted with molecular oxygen or a molecular oxygen-containing gas by gas-phase catalytic oxidation method to produce crude (meth)acrylic acid. More specifically, the crude (meth)acrylic acid may be produced by the method of producing (meth)acrolein from propylene (isobutylene or t-butanol in the case of methacrolein) as a raw material in the presence of a Mo—Bi-based composite oxide catalyst composed of Mo—Bi—Fe—Co—Ni—B—Na—Si—O, etc., and then subjecting the resultant (meth)acrolein to gas-phase catalytic oxidation reaction in the presence of a Mo—V-based composite oxide catalyst composed of Mo—V—Sb—Ni—Cu—Si—O, etc., or the method of subjecting propane as a raw material to gas-phase catalytic oxidation in the presence of a Mo—Bi—Te-based composite oxide catalyst, a Mo—Bi—Se-based composite oxide catalyst or the like. In the following descriptions, the production process of the present invention is explained concerning production of acrylic acid as a typical example. However, the production process of the present invention is also applicable to production of methacrylic acid.

The oxidation reaction may be conducted by one-pass method, unreacted propylene recycling method and combustion exhaust gas recycling method. The production process of the present invention may be conducted by any of these methods.

(1) One-pass Method:

The one-pass method is such a method in which in a front stage reaction, a mixed gas of propylene, air and steam is fed to convert the mixed gas into mainly acrolein and acrylic acid, and then the resultant outlet gas from the front stage reaction is fed to a rear stage reaction without separating the above reaction products therefrom. Upon feeding the outlet gas to the rear stage reaction, additional amounts of air and steam required in the rear stage reaction may be generally fed together with the outlet gas from the front stage reaction to the rear stage reaction.

(2) Unreacted Propylene Recycling Method:

In the unreacted propylene recycling method, an acrylic acid-containing reaction gas obtained in the rear stage reaction is introduced into an acrylic acid-collecting apparatus to collect acrylic acid in the form of an aqueous solution thereof, and a part of an exhaust gas containing unreacted propylene which is obtained in the collecting apparatus is supplied to the front stage reaction to recycle and reuse a part of the unreacted propylene therein.

(3) Combustion Exhaust Gas Recycling Method:

The combustion exhaust gas recycling method is such a method in which an acrylic acid-containing reaction gas obtained in the rear stage reaction is introduced into the acrylic acid-collecting apparatus to collect acrylic acid in the form of an aqueous solution thereof, and then a whole amount of the exhaust gas discharged from the collecting apparatus is combustion-oxidized to convert unreacted propylene or the like contained in the exhaust gas mainly into carbon dioxide and water, and a part of the thus obtained combustion exhaust gas is added and recycled to the front stage reaction.

Examples of the reactor used in the oxidation reaction may include fixed bed multipipe-type reactors, fixed bed plate-type reactors and fluidized bed-type reactors, though it is not limited to these reactors. Among these reactors, the fixed bed multipipe-type reactors have been extensively used to produce acrolein or acrylic acid by gas-phase catalytic oxidation reaction in which propylene or isobutylene is reacted with molecular oxygen or a molecular oxygen-containing gas in the presence of a composite oxide catalyst. The fixed bed multipipe-type reactors are not particularly restricted as long as these reactors are ordinarily usable in industrial applications.

Acrylic acid may be usually produced from the acrylic acid-containing gas obtained in the oxidation reaction by any of the following three methods.

(1) Method of contacting the acrylic acid-containing gas with water to collect acrylic acid in the form of an aqueous solution thereof; extracting acrylic acid from the thus obtained aqueous acrylic acid solution using an appropriate extraction solvent; then separating the resultant extract into acrylic acid and the solvent.

(2) Method of contacting the acrylic acid-containing gas with water to collect acrylic acid in the form of an aqueous solution thereof; distilling the thus obtained aqueous acrylic acid solution in the presence of an azeotropic solvent in an azeotropic separation column to azeotropically separate crude acrylic acid from a bottom of the column; and then removing acetic acid from the obtained crude acrylic acid.

(3) Method of contacting the acrylic acid-containing gas with an organic solvent to collect acrylic acid in the form of an organic solvent solution of acrylic acid, thereby simultaneously separating and removing water, acetic acid, etc., therefrom; and then separating acrylic acid from the thus obtained organic solvent solution of acrylic acid.

The water, acetic acid, organic solvent, solvent, azeotropic solvent (examples of these solvent may include methyl isobutyl ketone, methyl ethyl ketone, toluene, propyl acetate, ethyl acetate and mixed solvents of any two or more thereof), etc., may be separated using an ordinary distillation column. As the distillation column, there may be used distillation columns generally used in chemical plants, which are constituted of a single tower or two or more towers. The distillation column may be provided therein with trays or packing materials. The tray or packing materials used in the distillation column are not particularly restricted, and any ordinary trays and packing materials may be suitably used therein. These trays and packing materials may be used in the combination of any two or more kinds thereof.

Examples of the trays may include trays having a downcomer such as a bubble cap tray, a perforate-plate tray, a valve tray, a SUPERFRAC tray and a MAX-FRAC tray, and trays having no downcomer such as a dual flow tray. Examples of the packing material may include regular packing materials and irregular packing materials. Specific examples of the regular packing materials may include "SULZER PACKING" produced by Sulzer Brothers Limited, "SUMITOMO SULZER PACKING" produced by Sumitomo Jukikai Kogyo Co., Ltd., "MELLAPAK" produced by Sumitomo Jukikai Kogyo Co., Ltd., "GEM-PAK" produced by Grich Inc., "MONTZ-PAK" produced by Montz Inc., "GOODROLL PACKING" produced by Tokyo Special Wire Netting Co. Ltd., "HONEYCOMB PACK" produced by Nihon Gaishi Co., Ltd., "IMPULSE PACKING" produced by Nagaoka Co., Ltd., and "MC PACK" produced by Mitsubishi Chemical Engineering Co., Ltd. Specific examples of the irregular packing materials may include "INTERLOX SADDLES" produced by Norton Inc., "TELLERETT" produced by Nittetsu Kakoki Co., Ltd., "POLE RINGS" produced by BASF AG, "CASCADE MINI-RING" produced by Mass-Transfer Inc., and "FLEXI-RINGS" produced by Nikki Co., Ltd.

As a cooler attached to the distillation column, there may be used a top gas-cooling heat exchanger (condenser) and a vent gas-cooling heat exchanger (vent gas condenser), which can be attached to the distillation column. These condensers are generally classified into in-column installed condensers and out-of-column installed condensers. The type of the condenser and the vent gas condenser is not particularly restricted. Specific examples of these condensers may include vertical fixed pipe plate-type condensers, horizontal fixed pipe plate-type condensers, U-shaped pipe-type condensers, double pipe-type condensers, spiral-type condensers, pyramidal block-type condensers and plate-type condensers.

The heat exchanger (reboiler) attached to the distillation column for heating a bottom liquid thereof is generally classified into in-column installed reboilers and out-of-column installed reboilers. The type of the reboiler attached to the distillation column is not particularly restricted. Specific examples of the reboiler may include vertical fixed pipe plate-type reboilers, horizontal fixed pipe plate-type reboilers, U-shaped pipe-type reboilers, double pipe-type reboilers, spiral-type reboilers, pyramidal block-type reboilers, plate-type reboilers and thin-film evaporator-type reboilers.

The materials of various nozzles, column body, reboilers, condensers, vent gas condensers, conduits, supports, collision plates (including top plates), etc., of the distillation column are not particularly restricted, and may be appropriately selected according to properties of respective liquids to be treated, temperature conditions and anti-corrosion property. In the production of (meth)acrylic acid or (meth)acrylic esters, examples of the materials may include stainless steels such as SUS304, SUS304L, SUS316, SUS316L, SUS317, SUS317L and SUS327, hastelloys, or the like.

Since acrylic acid is an easily-polymerizable compound, it is preferred that the low-boiling components are removed from the reaction solution by adding a polymerization inhibitor thereto. Examples of the polymerization inhibitor may include copper acrylate, copper dithiocarbamates, phenol compounds and phenothiazine compounds. Specific examples of the copper dithiocarbamates may include copper dialkyldithiocarbamates such as copper dimethyldithiocarbamate, copper diethyldithiocarbamate, copper dipropyldithiocarbamate and copper dibutyldithiocarbamate; copper cyclic alkylenedithiocarbamates such as copper ethylenedithiocarbamate, copper tetramethylenedithiocarbamate, copper pentamethylenedithiocarbamate and copper hexamethylenedithiocarbamate; and copper cyclic oxydialkylenedithiocarbamates such as copper oxydiethylenedithiocarbamate. Specific examples of the phenol compounds may include hydroquinone, methoquinone, pyrogallol, catechol, resorcin, phenol and cresol. Specific examples of the phenothiazine compounds may include phenothiazine, bis-(α-methylbenzyl)phenothiazine, 3,7-dioctyl phenothiazine and bis-(α,α'-dimethylbenzyl)phenothiazine. These compounds may be used singly or in combination of any two or more thereof.

Next, the step (B) is explained. In the step (B), the crude (meth)acrylic acid is purified to produce high-purity (meth) acrylic acid (herein after referred as (meth)acrylic acid product). The step (B) usually includes a crude (meth)acrylic acid purification step (hereinafter, only crude acrylic acid is described as a typical example).

Crude Acrylic Acid Purification Step:

In the crude acrylic acid purification step, high-boiling components are removed from the crude acrylic acid to obtain high-purity acrylic acid. Examples of the high-boiling components may include aldehydes such as, for example, benzaldehyde and furfural, maleic acids such as, for example, maleic anhydride, Michael adducts of acrylic acid or the like. Examples of the Michael adducts may include acrylic dimers, acrylic trimers, acrylic tetramers or the like.

In the case where the crude acrylic acid contains the aldehydes and/or the maleic acids, the crude acrylic acid is preferably pretreated with an agent for removing the aldehydes and/or the maleic acids therefrom (refer to Japanese Patent Application Laid-open Nos. 2001-58970 and 2001-213839). More specifically, after a hydrazine compound is added to the crude acrylic acid to previously react the aldehydes and/or the maleic acids contained in the crude acrylic acid therewith, the crude acrylic acid is preferably subjected to distillation purification. The reaction apparatus used for the reaction between the aldehydes and/or the maleic acids contained in the crude acrylic acid and the hydrazine compound is not particularly restricted as long as it can ensure a temperature and a residence time required for the reaction. Examples of the reaction apparatus may include a reaction vessel equipped with a stirrer and a tube-type reaction vessel. The reaction temperature is preferably as low as possible, more specifically, in the range of from a melting point of acrylic acid to 50° C. The reaction time (residence time) is usually not less than 10 min, preferably 30 min to 3 hr.

Examples of the hydrazine compound may include hydrazine, hydrazine hydrate, phenyl hydrazine, hydrazine sulfate and hydrazine chloride. These hydrazine compounds may be used in the form of a mixture of any two or more thereof. The amount of the hydrazine compound added may be appropriately selected according to amounts of the aldehydes and/or the maleic acids as well as allowable concentrations of the aldehydes and/or the maleic acids contained in the high-purity acrylic acid obtained after distillation thereof.

The hydrazine compound is preferably directly added to the crude acrylic acid. The amount of the hydrazine compound added is usually 0.1 to 2 times by mole, preferably 0.5 to 2 times by mole, more preferably 0.5 to 1 time by mole based on the total amount of the aldehydes and the maleic acids contained in the crude acrylic acid.

The addition method of the hydrazine compound is not particularly restricted. Since the hydrazine compound is required to react with impurities to be removed, the residence time from addition of the hydrazine compound to the crude acrylic acid to production of purified (meth)acrylic acid as a distillate from a top of the distillation column is preferably 10 min to 5 hr, more preferably 20 min to 3 hr.

When the reaction time (residence time) is too short, the hydrazine compound may fail to sufficiently react with the impurities. On the other hand, when the reaction time (residence time) is too long, there is such a risk that the amount of impurities is increased owing to decomposition of the reaction product. Therefore, the reaction time (residence time) is preferably selected from the above-specified range.

Also, in addition to the hydrazine compound, the aldehydes may be removed from the crude acrylic acid using a mercaptan compound such as n-butyl mercaptan, n-octyl mercaptan and n-dodecyl mercaptan. More specifically, a liquid prepared by adding the mercaptan compound to the crude acrylic acid may be passed through a resin column filled with a sulfonic acid-type cation exchange resin at a temperature of 20 to 90° C. at a space velocity (SV) of 0.1 to 10/hr to remove the aldehydes therefrom. The passage of the liquid through the resin column may be conducted by either a down flow method or an up flow method. The above aldehyde-removing agent may be used in an amount of usually 1 to 8 moles based on one mole of the aldehydes to be removed.

The crude acrylic acid treated with the hydrazine compound and/or the mercaptan compound may be usually purified in a distillation column by adding a polymerization inhibitor such as, for example, copper acrylate and copper dithiocarbamate. As the polymerization inhibitor, there may be used the same polymerization inhibitors as used in the step (A). High-purity acrylic acid is distilled out from a top of the distillation column, whereas high-boiling components remain in a bottom liquid. The distillation method is not particularly restricted, and there may be used various distillation methods such as single distillation and precision distillation. In addition, the distillation procedure may be conducted by either a continuous method or a batch method.

Meanwhile, although the method of purifying the crude acrylic acid by distillation is explained above, in the present invention, there may also be adopted the method of purifying the crude acrylic acid by crystallization.

Next, the step (C) is explained. In the step (C), the crude (meth)acrylic acid is reacted with alcohols to produce (meth)acrylic esters. Specifically, the step (C) includes an esterification reaction step of reacting the crude (meth)acrylic acid with alcohol in the presence of an acid catalyst, and a (meth)acrylic ester purification step of conducting unit procedures for concentrating the resultant reaction solution containing crude (meth)acrylic esters, such as extraction, evaporation and distillation. Examples of the (meth)acrylic esters produced according to the process of the present invention may include methyl (meth)acrylate, ethyl (meth) acrylate, butyl (meth)acrylate, isobutyl (meth)acrylate, tert-butyl (meth)acrylate, 2-ethylhexy (meth)acrylate, 2-hydroxyethyl (meth)acrylate, 2-hydroxypropyl (meth)acrylate and methoxyethyl (meth)acrylate.

Esterification Reaction Step:

The alcohols used in the esterification reaction step may be selected from those corresponding to the aimed esters. Examples of the alcohols may include methanol, ethanol, propanol, isopropanol, n-butanol, i-butanol, sec-butanol, t-butanol, 2-ethylhexyl alcohol, 2-hydroxyethyl alcohol, 2-hydroxypropyl alcohol and methoxyethyl alcohol.

Examples of the acid catalyst may include homogeneous acid catalysts and heterogeneous solid acid catalysts. Specific examples of the homogeneous acid catalysts may include sulfuric acid, p-toluenesulfonic acid and methanesulfonic acid. Specific examples of the heterogeneous solid acid catalysts may include strong acid cation exchange resins, activated clay and acidic zeolite. The strong acid cation exchange resins may be of either a porous type or a gel type, and the crosslinking degree thereof is usually 2 to 16%. Examples of suitable commercial products of the strong acid cation exchange resins may include porous strong acid cation exchange resins "PK-208", "PK-216" and "PK-228" produced by Mitsubishi Kagaku Co., Ltd., etc.

The esterification reaction may be conducted by conventionally known methods without any particular limitation. The industrial production method may be either a batch method or a continuous method. The molar ratios of raw materials used in the esterification reaction, kind and amount of catalyst used therein, reaction method, reaction conditions, etc., may be appropriately selected according to kinds of alcohols used therein. In addition, upon the above reaction and distillation, an oxygen-containing gas as a polymerization inhibitor may be added to the reactor, distillation column, etc., in order to prevent occurrence of polymerization of (meth)acrylic acid and (meth)acrylic esters as reaction products.

(Meth)Acrylic Ester Purification Step:

The crude (meth)acrylic esters obtained in the above esterification reaction are purified by unit procedures such as extraction, evaporation and distillation. The distillation column (purification column) usable in the respective unit procedures may be the same as explained in the step (A). The conditions of the respective unit procedures may be appropriately selected according to molar ratios between (meth)acrylic acid and alcohol as raw materials used in the esterification reaction, kind of catalyst used in the esterification reaction as well as respective properties of the raw materials, reaction by-products and (meth)acrylic esters. Through the above respective unit procedures, (meth)acrylic esters as aimed products are obtained from a top of the (meth)acrylic ester purification column.

The bottom liquid obtained from the purification column contains mainly the polymerization inhibitor and Michael adducts. Examples of the Michael adducts may include such Michael adducts obtained by adding acrylic acid to the above acrylic esters such as alkyl (having 2 to 8 of carbon atoms) esters or cycloalkyl esters of acrylic acid, specifically, β-acryloxypropionic esters; Michael adducts of alcohols, specifically, β-alkoxypropionic esters; esters of acrylic dimers, trimers or tetramers; β-hydroxypropionic acid; and β-hydroxypropionic esters. For this reason, the bottom liquid is preferably fed as a high-boiling liquid to a high-boiling component separation column to recover and reuse these valuable substance.

Next, the tank for temporarily storing the crude (meth)acrylic acid is explained. It is preferred that the tank has a capacity capable of storing such an amount of the crude (meth)acrylic acid as produced for 5 to 10 days in the step (A). The crude (meth)acrylic acid produced in the step (A) is fed directly through a conduit and/or through the tank, into the respective steps (B) and (C). Under ordinary operation conditions, the amount of the crude (meth)acrylic acid stored in the tank may be controlled to 40 to 60%. For this purpose, the operational load of each of the steps (B) and (C) may be adjusted such that the amount of the crude (meth)acrylic acid produced in the step (A) is well-balanced with the amount of the crude (meth)acrylic acid consumed in the steps (B) and (C).

In the case where the operation of the plant used in the step (B) or (C) is stopped due to occurrence of troubles therein, the crude (meth)acrylic acid to be fed to the stopped plant is temporarily stored in the tank. The time required for repairing the stopped plant used in the step (B) or (C) is within one day at the earliest and about 7 days at the latest.

The present invention is characterized in that in the process for producing (meth)acrylic acid and (meth)acrylic esters which is conducted using the plants for the steps (A), (B) and (C) as well as the tank, these facilities are designed such that the production capacity of the plant used in the step (A) (i.e., maximum feed amount of the crude (meth)acrylic acid) is lower than a total consumption capacity of the plants used in the steps (B) and (C) (i.e., maximum consumption amount of the crude (meth)acrylic acid).

Owing to the above feature of the present invention, the plants used in the steps (B) and/or (C) can afford to consume the surplus acrylic acid by such an amount corresponding to the capacity higher than that of the step (A). Therefore, the surplus crude (meth)acrylic acid stored in the tank can be suitably treated, namely can be consumed and reduced without any substantial change in operational load of the plant used in the step (A). As a result, even when the plant used in the step (B) or (C) is stopped due to occurrence of troubles therein, the plant used in the step (A) can be continuously operated without any change in operational load thereof, so that any polymerization troubles due to change in operational load of the step (A) can be prevented from occurring.

In the case where the production capacity of the plant used in the step (A) is identical to or larger than the total consumption capacity of the plants used in the steps (B) and (C), it may be difficult to suitably treat the surplus crude (meth)acrylic acid stored in the tank. As a result, in order to reduce the amount of the surplus crude (meth)acrylic acid, it is required to reduce the operational load of the plant used in the step (A). The production capacity of the plant used in the step (A) is preferably not more than 97%, more preferably 70 to 90% based on the total consumption capacity of the plants used in the steps (B) and (C). When the production capacity of the plant used in the step (A) is less than 70%, it may be sometimes rather preferred to dispose an additional one series of plant for the step (A). The capacities of the plants used in the respective steps (A), (B) and (C) are not particularly restricted, and the production capacity of the plant used in the step (A) for producing the crude (meth)acrylic acid is usually not less than 30000 tons per year.

EXAMPLES

The present invention is described in more detail by Examples, but the Examples are only illustrative and not intended to limit the scope of the present invention.

Example 1

A plant for production of acrylic acid and methyl acrylate including a crude acrylic acid production plant (corresponding to the step (A); hereinafter referred to merely as "plant A"), a high-purity acrylic acid plant (corresponding to the step (B); hereinafter referred to merely as "plant B"), an acrylic ester plant (corresponding to the step (C); hereinafter referred to merely as "plant C"), and an acrylic acid storage tank, was designed such that the respective plants had the below-mentioned capacities. Meanwhile, the plant (A) was constituted of a multipipe type reactor, an absorption column, an azeotropic separation column, an acetic acid separation column and a crude acrylic acid column; the plant (B) was constituted of a reactor and a high-purity acrylic acid purification column; and the plant (C) was constituted of a reactor, an acrylic acid separation column, an extraction column, an alcohol recovery column, a low-boiling component separation column and an ester purification column.

The plant (A) had a crude acrylic acid production capacity of 14 ton/hour, the plant (B) had a crude acrylic acid consumption capacity of 6 ton/hour, and the plant (C) had a crude acrylic acid consumption capacity of 10 ton/hour. The crude acrylic acid produced in the plant (A) was temporarily fed to the acrylic acid storage tank, and then fed from the acrylic acid storage tank to the plants (B) and (C) through respective conduits.

In the plant (A), an acrylic acid aqueous solution (containing 55% by weight of acrylic acid and 1.5% by weight of acetic acid) obtained in the absorption column was fed to the azeotropic separation column. The azeotropic separation column was operated at a bottom temperature of 83° C. and a top temperature of 44° C. while controlling a top pressure thereof to 14 kPa. Since operation of the plant (B) had to be stopped due to occurrence of troubles therein, the supply of the crude acrylic acid from the tank to the plant (B) was terminated, but the plants (A) and (C) were continuously operated. The plant (A) was operated at an operation load of 100%, and a part of the crude acrylic acid produced in the plant (A) was consumed in the plant (C), whereas a surplus of the crude acrylic acid to be consumed in the plant (B) was stored in the tank. When the plant (B) was restored after 7 days, the amount of the crude acrylic acid stored in the tank was increased from initial 50% to 85%.

While continuously operating the plant (A) at an operation load of 100% (crude acrylic acid production capacity: 14 ton/hour), the plant (B) was operated at an operational load of 100% (crude acrylic acid consumption capacity: 6 ton/hour) and the plant (C) was operated at an operational load of 100% (crude acrylic acid consumption capacity: 10 ton/hour), so that the amount of the crude acrylic acid stored in the tank was reduced to 50%. Thereafter, the operational load of the plant (C) was changed to 80% at which operation of the plant (C) was continued. As a result, it was confirmed that the troubles of operation of the plant (B) were overcome and the amount of the crude acrylic acid stored in the tank was restored (reduced) to an ordinary level without change in operational load of the plant (A). After 3 months from the stoppage of operation of the plant (B), the plant was stopped for periodic inspection to overhaul and inspect an inside of the azeotropic separation column (dehydration column). As a result, it was confirmed that no polymers of acrylic acid were recognized therein.

Comparative Example 1

The same procedure as defined in Example 1 was conducted except that the crude acrylic acid consumption capacity of the plant (C) was changed to 8 ton/hour and the other plants had the same capacities as those used in Example 1. Since operation of the plant (B) had to be stopped due to occurrence of troubles therein, the supply of the crude acrylic acid from the tank to the plant (B) was terminated, but the plants (A) and (C) were continuously operated. The plant (A) was operated at an operation load of 100%, and a part of the crude acrylic acid produced in the plant (A) was consumed in the plant (C), whereas a surplus of the crude acrylic acid to be consumed in the plant (B) was stored in the tank. When the plant (B) was restored after 7 days, the amount of the crude acrylic acid stored in the tank was increased from initial 50% to 85%.

After restoring the plant (B), the plants (A), (B) and (C) were respectively operated at an operational load of 100%. However, since such an operation of these plants failed to restore (reduce) the amount of the crude acrylic acid stored in the tank to an ordinary level, the operational load of the plant (A) was reduced to 70%. After the amount of the crude acrylic acid stored in the tank was reduced to the ordinary level, the operational load of the plant (A) was raised again to 100% and continuously operated. From the time at which the operational load of the plant (A) was reduced to 70%, the differential pressure between the top and bottom of the azeotropic separation column (dehydration column) was gradually increased, and after 2 months, a continuous operation of the plant (A) became impossible. As a result of overhauling the azeotropic separation column (dehydration column) to inspect an inside thereof, it was confirmed that a large amount of polymers was recognized on 1- to 4-stage trays.

The invention claimed is:

1. A process for producing (meth)acrylic acid and (meth)acrylic esters comprising the steps of:
    (A) reacting propane, propylene, or isobutylene and/or (meth)acrolein, with molecular oxygen or a molecular oxygen-containing gas by gas-phase catalytic oxidation method to produce crude (meth)acrylic acid;
    (B) purifying the resultant crude (meth)acrylic acid to produce a (meth)acrylic acid product; and
    (C) reacting the crude (meth)acrylic acid with alcohol to produce (meth)acrylic esters,
    in case of stopping a plant used in any one of the steps (B) and (C) disposed in parallel with each other, a resultant surplus crude (meth)acrylic acid being temporarily stored in a tank, and after restoring the stopped plant, the crude (meth)acrylic acid stored in a tank being fed to the plant used in the step (B) and/or the plant used in the step (C),
    wherein a production capacity of the plant used in the step (A) is designed so as to be lower than a total consumption capacity of the plants used in the steps (B) and (C).

* * * * *